(12) United States Patent
Jalkanen et al.

(10) Patent No.: US 12,015,449 B2
(45) Date of Patent: Jun. 18, 2024

(54) SENSING APPARATUS AND SYSTEM

(71) Applicant: Nokia Technologies Oy, Espoo (FI)

(72) Inventors: Jukka Mikael Jalkanen, Helsinki (FI); Michel Rene Gustave Ghislain Gillet, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 151 days.

(21) Appl. No.: 16/772,114

(22) PCT Filed: Dec. 14, 2018

(86) PCT No.: PCT/EP2018/084909
§ 371 (c)(1),
(2) Date: Jun. 11, 2020

(87) PCT Pub. No.: WO2019/129505
PCT Pub. Date: Jul. 4, 2019

(65) Prior Publication Data
US 2021/0091860 A1    Mar. 25, 2021

(30) Foreign Application Priority Data

Dec. 29, 2017    (EP) ..................................... 17211188

(51) Int. Cl.
*H04B 10/40*    (2013.01)
*A61B 5/00*    (2006.01)
(Continued)

(52) U.S. Cl.
CPC ......... *H04B 10/807* (2013.01); *A61B 5/0017* (2013.01); *A61B 5/01* (2013.01);
(Continued)

(58) Field of Classification Search
CPC .. H04B 10/807; H04B 10/25; H04B 10/2589; H04B 10/40; H04B 10/806;
(Continued)

(56) References Cited

U.S. PATENT DOCUMENTS 4,987,579 A * 1/1991 Yoshinaka ............. G01K 1/024
                                                  374/E1.004
5,119,679 A * 6/1992 Frisch ................... G01L 19/069
                                                  250/227.21
(Continued)

FOREIGN PATENT DOCUMENTS

CN          106644166 A    5/2017
EP           0043929 A2    1/1982
(Continued)

OTHER PUBLICATIONS

Gordon, Signal Encoding Techniques, Dec. 2008, ICT SIIT, All Document. https://sandilands.info/sgordon/teaching/its323y07s1/protected/ITS323Y07S1L06-SignalEncodingTechniques.pdf (Year: 2008).*

(Continued)

*Primary Examiner* — Dibson J Sanchez
(74) *Attorney, Agent, or Firm* — Harrington & Smith (57) ABSTRACT

An apparatus and sensing system wherein the apparatus comprises: sensing means configured to sense a parameter; optical output means configured to provide an optical output signal indicative of data obtained by the sensing means; optical input means configured to receive an optical input signal and convert the optical input signal to electrical power; and storage means configured to store the electrical power obtained by the optical input means and enable the power to be provided to the sensing means and the optical output means; and wherein the optical output means comprises one or more light emitting diodes and optical coupling means where the optical coupling means are configured to couple the apparatus to a processing device to enable data obtained by the sensing means to be transmitted to the processing device.

17 Claims, 3 Drawing Sheets

(51) Int. Cl.
  *A61B 5/01* (2006.01)
  *H04B 10/80* (2013.01)
  *H04B 10/25* (2013.01)
(52) U.S. Cl.
  CPC .... *A61B 5/6804* (2013.01); *A61B 2562/0271* (2013.01); *A61B 2562/146* (2013.01); *H04B 10/25* (2013.01); *H04B 10/2589* (2020.05); *H04B 10/40* (2013.01); *H04B 10/806* (2013.01)
(58) Field of Classification Search
  CPC ....... A61B 5/0017; A61B 5/01; A61B 5/6804; A61B 2562/0271; A61B 2562/146; A61B 5/6801; A61B 5/02438; A61B 5/443; A61B 2560/0214
  USPC .................................................. 398/135–172
  See application file for complete search history.

(56) References Cited

U.S. PATENT DOCUMENTS

| | | | | |
|---|---|---|---|---|
| 5,528,409 | A * | 6/1996 | Cucci | H04B 10/807 398/171 |
| 6,221,025 | B1 * | 4/2001 | Skoletsky | A61B 5/026 600/549 |
| 7,366,021 | B2 * | 4/2008 | Taylor | G11C 7/067 365/185.21 |
| 7,528,760 | B2 * | 5/2009 | Forejt | H03M 1/504 341/166 |
| 7,696,901 | B2 * | 4/2010 | Wilson | E21B 47/135 398/171 |
| 7,806,603 | B2 * | 10/2010 | Izumo | G08C 23/06 385/89 |
| 8,180,225 | B2 * | 5/2012 | Werthen | G06F 13/385 398/171 |
| 8,466,690 | B2 * | 6/2013 | Stewart | G01R 31/1272 324/551 |
| 8,573,843 | B2 * | 11/2013 | Tsuchida | G01K 13/20 374/185 |
| 9,979,480 | B1 | 5/2018 | Schubert | H04B 10/807 |
| 10,598,537 | B2 * | 3/2020 | Crowne | G01F 23/241 |
| 2005/0190093 | A1 * | 9/2005 | Mayer | H03M 3/32 341/155 |
| 2007/0273411 | A1 * | 11/2007 | Harris | H03F 3/45475 327/103 |
| 2007/0295713 | A1 * | 12/2007 | Carlton-Foss | G01K 1/16 219/497 |
| 2009/0016715 | A1 * | 1/2009 | Furey | H04B 10/807 398/38 |
| 2009/0299682 | A1 * | 12/2009 | Yarden | G01K 7/42 702/131 |
| 2011/0237916 | A1 * | 9/2011 | Hanson | A61B 5/14532 600/365 |
| 2012/0197094 | A1 * | 8/2012 | Zhang | A61B 6/04 600/300 |
| 2015/0180425 | A1 * | 6/2015 | Lukashevich | H01L 27/1203 330/289 |
| 2016/0231183 | A1 * | 8/2016 | Keuten | G01K 1/08 |
| 2016/0256055 | A1 | 9/2016 | Okamura | |
| 2016/0274546 | A1 * | 9/2016 | Kurose | G04F 10/005 |
| 2017/0127944 | A1 | 5/2017 | Sun | |
| 2017/0272157 | A1 * | 9/2017 | Crowne | H04B 10/25 |
| 2017/0338889 | A1 * | 11/2017 | Dinh | H04Q 9/00 |
| 2018/0168508 | A1 * | 6/2018 | Biel | A61B 5/6843 |

FOREIGN PATENT DOCUMENTS

| | | |
|---|---|---|
| EP | 1703360 A2 | 9/2006 |
| WO | 2006/027586 A1 | 3/2006 |

OTHER PUBLICATIONS

Chen et al., "A Time-to-Digital-Converter-Based CMOS Smart Temperature Sensor", IEEE Journal of Solid-State Circuits, vol. 40, No. 8, Aug. 2005, pp. 1642-1648.

Mohamad et al., "A Low Power Temperature Sensor based on a Voltage to Time Converter Cell", 25th International Conference on Microelectronics (ICM), 2013, 4 pages.

Kamakshi et al., "A 0.2 V, 23 nW CMOS Temperature Sensor for Ultra-Low-Power IoT Applications", J. Low Power Electron. Appl., vol. 6, 2016, pp. 1-16.

"Linear Optical Isolation for Safe Sensor Operation", Digi-Key Electronics, Retrieved on Jun. 11, 2020, Webpage available at : https://www.digikey.in/en/articles/linear-optical-isolation-for-safe-sensor-operation.

Extended European Search Report received for corresponding European Patent Application No. 17211188.2, dated Jun. 21, 2018, 9 pages.

International Search Report and Written Opinion received for corresponding Patent Cooperation Treaty Application No. PCT/EP2018/084909, dated Feb. 19, 2019, 11 pages.

* cited by examiner

SENSING APPARATUS AND SYSTEM

RELATED APPLICATION

This application claims priority to PCT Application No. PCT/EP2018/084909, filed on Dec. 14, 2018, which claims priority to European Application No. 17211188.2, filed on Dec. 29, 2017, each of which is incorporated herein by reference in its entirety.

TECHNOLOGICAL FIELD

Examples of the disclosure relate to a sensing apparatus and system. In particular, they relate to a sensing apparatus and system which can be worn by a subject.

BACKGROUND

Apparatus that can be used for sensing are known. Such apparatus could be wearable apparatus that may be worn by the subject. This may enable parameters such as the temperature of the subject, the humidity of the subject's skin, the presence of chemicals or analytes in the environment around the subject, or any other suitable parameters to be monitored for extended periods of time.

BRIEF SUMMARY

According to various, but not necessarily all, examples of the disclosure there is provided an apparatus comprising: sensing means configured to sense one or more parameters; optical output means configured to provide an optical output signal indicative of data obtained by the sensing means; optical input means configured to receive an optical input signal and convert the optical input signal to electrical power; and storage means configured to store the electrical power obtained by the optical input means and enable the power to be provided to the sensing means and the optical output means; wherein the optical output means comprises one or more light emitting diodes and optical coupling means where the optical coupling means are configured to couple the apparatus to a processing device to enable data obtained by the sensing means to be transmitted to the processing device.

The optical input means may comprise one or more photodiodes and optical coupling means where the optical coupling means are configured to enable light from a processing device to be detected by the one or more photodiodes.

The optical coupling means may comprise at least one bi-directional light guide.

There might be no direct electrical connection between the apparatus and the processing device.

The apparatus may be thermally insulated from the processing device.

The apparatus may be comprised within a separate device to the processing device.

The sensing means may comprise digital sensing means configured to provide a digital output. The optical coupling means may be configured to receive a control signal from the processing device to control the digital sensing means.

The apparatus may comprise voltage to time conversion means configured to convert an analogue output of the sensing means to a digital output.

The storage means may comprise a super capacitor.

The sensing means may comprise temperature sensing means.

The temperature sensing means may be thermally insulated from the optical output means and the optical input means.

The apparatus may be comprised within a wearable device.

The sensing means may be configured to directly contact a subject in use.

The optical coupling means may comprise a first optical coupling means and a second optical coupling means; wherein the first optical coupling means are configured to enable the data obtained by the sensing means to be transmitted to the processing device; and wherein the second optical coupling means are configured to enable the light from the processing device to be detected by the one or more photodiodes.

According to various, but not necessarily all, examples of the disclosure there is provided a sensing system comprising an apparatus described above and a processing device.

The processing device may be comprised within a wearable device.

According to various, but not necessarily all, examples of the disclosure there is provided an apparatus comprising: one or more sensors configured to sense a parameter; an optical output configured to provide an optical output signal indicative of data obtained by the one or more sensors; an optical input configured to receive an optical input signal and convert the optical input means to electrical power; and a power source configured to store the electrical power obtained by the optical input and enable the power to be provided to the one or more sensors and the optical output; wherein the optical output comprises one or more light emitting diodes and one or more optical coupling components where the optical coupling components are configured to couple the apparatus to a processing device to enable data obtained by the one or more sensors to be transmitted to the processing device.

According to various, but not necessarily all, examples of the disclosure, there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Examples of the disclosure relate to a sensing apparatus 1 and system 21. The sensing apparatus 1 can be worn by a subject. This could enable an accurate measurement of parameters relating to the subject, such as the subject's temperature, to be made. In examples of the disclosure the sensing apparatus 1 is configured to send data to a processing device 23 via an optical output 5. The sensing apparatus 1 may also obtain power and/or control signals, from the processing device 23, via an optical input 7. This enables the sensing apparatus 1 to be thermally insulated from the processing device 23 because there is no need for any direct electrical connection between the sensing apparatus 1 and the processing device 23. This may improve the accuracy of measurements made by the sensing apparatus 1.

Figure 1:
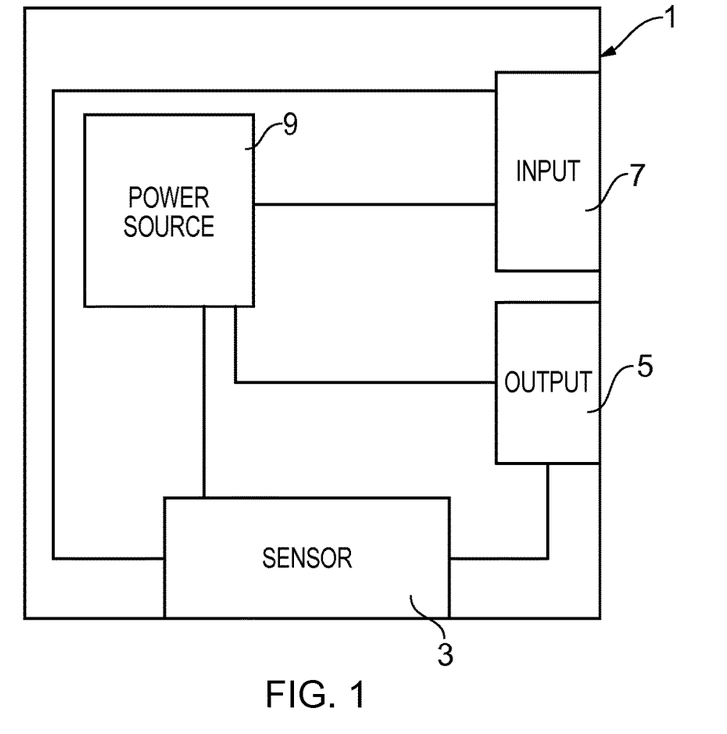
FIG. 1 illustrates an apparatus.

FIG. 1 schematically illustrates an apparatus 1 according to examples of the disclosure. The apparatus 1 is a sensing apparatus 1. The apparatus 1 comprises one or more sensors 3, an optical output 5, an optical input 7 and a power source 9.

The one or more sensors 3 may provide sensing means. The one or more sensors 3 may comprise any means which may be configured to sense a parameter. The sensors 3 may be configured to provide an electrical output signal dependent upon the parameter.

In some examples the parameter may comprise a biometric parameter of a subject. The biometric parameter may comprise any time varying signal that is generated by the subject's body. The biometric parameter may comprise an autonomic parameter. The autonomic parameter may be controlled subconsciously by the subject. The biometric parameters could comprises temperature, humidity, blood oxygen levels, hear rate, audio signals, pressure, presence of one or more analytes or any other suitable parameters.

In some examples the parameter could comprise a parameter of the environment in which the subject is located. For example, the parameter could comprise the ambient temperature, the presence of humidity or other chemicals, ambient light, electromagnetic radiation levels, noise or any other suitable parameter.

In some examples the one or more sensors 3 may comprise one or more temperature sensors. The one or more temperature sensors 3 could comprise any suitable type of sensors. The one or more temperature sensors 3 could comprise, thermistors, resistance temperature detectors, diodes, an integrated thermometer circuit, a digital thermometer configured to provide a digital output or any other suitable type of temperature sensors. Other types of temperature sensors 3 could be used in other examples of the disclosure.

Figure 4:
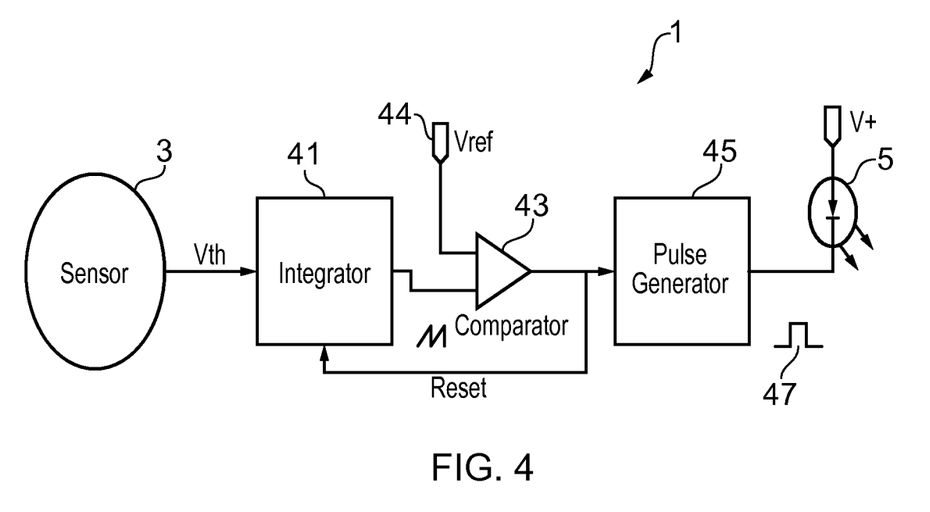
FIG. 4 illustrates components of an apparatus.

In examples where the one or more sensors 3 provide an analogue output the apparatus 1 may also comprise an analogue to digital converter. For example, where the one or more sensors 3 comprises an integrated thermometer circuit an analogue to digital converter may be provided to enable a digital output comprising the data obtained by the integrated thermometer circuit to be provided. The analogue to digital converter could be a voltage to time converter or any other suitable type of converter. An example of a voltage to time converter that could be used in some examples of the disclosure is shown in FIG. 4.

The one or more sensors 3 are configured to enable the parameters relating to a subject to be measured. The subject could be a person or animal who is wearing the apparatus 1. The one or more sensors 3 may may be positioned within the apparatus 1 so that when a subject wears the apparatus 1 the one or more sensors 3 are positioned adjacent, or in close proximity to, the skin of the subject. In some examples the one or more sensors 3 may be positioned within the apparatus 1 so that they are in direct contact with the skin of the subject. This enables the one or more sensors 3 to directly contact the subject when the apparatus 1 is in use.

In other cases a protective layer may be provided between the one or more sensors 3 and the skin of the subject. The protective layer could be configured to enable the parameter that is to be sensed to pass through the protective layer so that it can be sensed by the one or more sensors 3. For example where the one or more sensors 3 comprise a temperature sensor the protective layer may be thermally conductive. Similarly, where the one or more sensors 3 comprise a humidity sensor the protective layer may be permeable to water.

The one or more sensors 3 are coupled to the optical output 5. This may enable data obtained by the one or more sensors 3 to be provided to the optical output 5.

The optical output 5 comprises means for converting an electrical signal received from the one or more sensors 3 into an optical output signal. The optical output signal could comprise infrared light, light in the visible range of the spectrum or light having any other suitable frequency.

Figure 2:
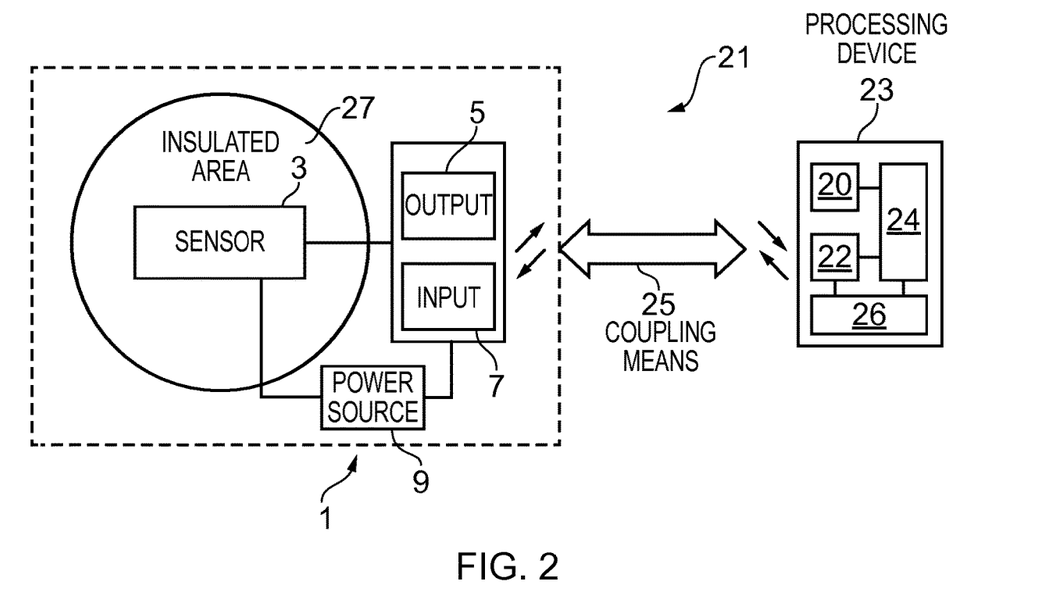
FIG. 2 illustrates a system.

The optical output 5 could comprise one or more light emitting diodes and optical coupling means. The optical coupling means comprises one or more optical components that are configured to optically couple the apparatus 1 to a processing device 23. This enables an optical output signal that is transmitted by the apparatus 1 to be received by a processing device 23. This enables data obtained by the one or more sensors 3 to be transmitted to the processing device 23. An example processing device 23 is shown in FIG. 2.

The apparatus 1 also comprises an optical input 7. The optical input 7 comprises means for converting an optical input signal into an electrical signal. The optical input signal could be received from the processing device 23 or any other suitable device. The optical input 7 may comprise control signals received from the processing device 23.

The optical input 7 may be coupled to the one or more sensors 3 to enable a control signal received via the optical input 7 to be provided to the one or more sensors 3. The control signal may trigger the one or more sensors 3 to make a reading. This may enable the one or more sensors 3 to be remotely controlled by the processing device 23 via the optical input 7.

The optical input 7 could comprise one or more photodiodes and optical coupling means. The optical coupling means comprises one or more optical components that are configured to optically couple the apparatus 1 to a processing device 23. This enables an optical output signal that is transmitted by the processing device 23 to be received by the apparatus 1. This enables data from the processing device 23, or any other suitable device, to be detected by the one or more photodiodes.

In some examples the same optical coupling means could be coupled to both the optical input 7 and the optical output 5. In other examples a separate optical coupling means could be provided for the optical output 5 and the optical input 7.

The power source 9 comprises storage means for storing energy which may be used to power the apparatus 1. The optical input 7 may also be coupled to the power source 9. This may enable signals received via the optical input 7 to be used to charge to power source 9. The power source 9 could be a low leakage capacitor, a super capacitor or any other suitable energy storage means.

The power source 9 is coupled to the one or more sensors 3 and the optical output 5 to enable power to be provided from the power source 9 to the one or more sensors 3 and the optical output 5.

The apparatus 1 may be provided within a wearable device. This could enable the apparatus 1 to be used for an extended period of time. For example the wearable device could be worn for a period of hours of even days and data relating to the subject and/or the environment around the subject could be collected throughout that time.

The wearable device could be attached to a strap which could be wrapped around the torso, or any other suitable part of the subject's body. In some examples the apparatus 1 could be provided within a wearable garment, such as a shirt, which could be worn by the subject. In some examples the apparatus 1 could be detached from the strap or garment in order to enable the strap or garment to be washed or otherwise cleaned.

In some examples the apparatus 1 could be provided within a sensing pad that could be adhered or otherwise attached to the subject's body. Other means for enabling a subject to wear the apparatus 1, or attaching the apparatus to a subject's body, could be used in other examples of the disclosure.

It is to be appreciated that the apparatus 1 may comprise additional components that are not shown in FIG. 1. For example, the apparatus 1 could comprise one or more additional sensors which could be configured to detect other biometric parameters such as heart rate, or other parameters relating to the subject. This may enable the same sensing apparatus 1 to be used to detect a plurality of different parameters.

As mentioned above the optical output 5 enables the apparatus 1 to transmit data from the one or more sensors 3 to a processing device 23. This may enable the processing device 23 to store the data obtained from the one or more sensors 3 and/or perform processing on the data. FIG. 2 illustrates an example sensing system 21 comprising an apparatus 1, optical coupling means 25 and a processing device 23.

The apparatus 1 may be an apparatus as shown in FIG. 1. Corresponding reference numerals are used for corresponding features.

In the example apparatus 1 in FIG. 2 the one or more sensors 3 are provided within an insulated area 27 and the other components of the apparatus 1, including the optical output 5, the optical input 7 and the power source 9 are provided outside of the insulated area 27. The one or more sensors 3 provided within the insulated area 27 could comprise one or more temperature sensors 3 or any other type of sensor s which may be sensitive to temperature.

One or more electrical connections may be provided through the insulated area 27. The electrical connections may be between the one or more sensors 3 and the other components of the apparatus 1. The electrical connections provided through the insulated area may be as short and thin as possible to reduce the amount of heat transferred to the one or more sensors 3.

The insulated area 27 ensures that the one or more sensors 3 are thermally insulated from the optical output 5, the optical input 7 and the power source 9. This prevents any heating of the other components of the apparatus 1 such as the optical output 5, the optical input 7 and the power source 9 from affecting the measurements made by the one or more sensors 3. This therefore may improve the accuracy of the measurements made by the one or more sensors 3.

It is to be appreciated that in other examples the apparatus 1 could be configured differently. For instance, in some examples the optical output 5 and/or the optical input 7 could be provided within the thermally insulated area 27. This configuration could be used where the power generated by the other components of the apparatus 1 is not high enough to cause a significant error in the measurements made by the one or more sensors 3.

The thermally insulated area 27 may comprise an area of the apparatus 1 which is surrounded by, or at least partially surrounded by, a thermally insulating material. The thermally insulating material could comprise a polymer or any other suitable insulating material.

The optical coupling means 25 provide means for coupling the apparatus 1 to a processing device 23. The optical coupling means 25 comprises one or more optical components which provide a channel though which the optical signals can be transmitted and/or received. In some examples the optical coupling means may comprise one or more light guides. In some examples the optical coupling means 25 may comprise at least one bi-directional light guide. In some examples different light guides could be coupled to the optical input 7 and the optical output 5. In other examples the same light guide could be coupled to both the optical input and the optical output 5.

In the example system 21 of FIG. 2 the system comprises one optical coupling means 25. In other examples the system 21 could comprise a plurality of optical coupling means. The plurality of optical coupling means 25 could comprise a first optical coupling means and a second optical coupling means. The first optical coupling means may be configured to enable the data obtained by the one or more sensors 3 to be transmitted to the processing device 23. The second optical coupling means may be configured to enable light from the processing device to be transmitted to the one or more photodiodes in the optical input 7.

The optical coupling means 25 does not contain any electrical connections. That is there is no path for direct current provided via the optical coupling means 25. There is no galvanic connection between the apparatus 1 and the processing device 23. This means that there is no heating of the apparatus 1 caused by any electrical connections to the processing device 23. Also there is no heat transferred via the electrical connections.

The optical coupling means 25 may act to thermally insulate the apparatus 1 from the processing device 23. That is the optical coupling means 25 may comprise a thermally insulating material so as to prevent heat from the processing device 23 from being transferred to the apparatus 1.

The processing device 23 could also be a wearable device. For instance, the processing device 23 could be attached to a strap which could be wrapped around the torso, or any other suitable part of the subject's body. The apparatus 1 could be attached to the same strap as the processing device 23. The apparatus 1 and the processing device 23 could be provided at different locations along the same strap. In some examples the processing device 23 could be provided within a wearable garment, such as a shirt, which could be worn by the subject. In such examples the apparatus 1 and the processing device 23 could be provided at different locations within the wearable garment.

In other examples the processing device 23 could be a device that is not worn by the subject. For example, it could be a computer, a mobile phone, a table or other suitable electronic device. This processing device could be configured to be coupled to the apparatus 1 to enable data from the apparatus 1 to be transmitted to the processing device 23.

The processing device 23, as shown in FIG. 2 comprises any suitable components which are needed to receive data from the apparatus 1 and perform any necessary processing on the data to enable an output indicative of the sensed parameter to be provided.

In the example of FIG. 2 the processing device 23 comprises an optical input 20, an optical output 22, controlling circuitry 24 and a main power source 26.

The optical input 20 comprises means for converting an optical input signal into an electrical signal. The optical input signal could be received from the apparatus 1 and may contain data obtained by the one or more sensors 3. This may enable the processing device 23 to obtain data indicative of the sensed parameter.

The optical input 20 could comprise one or more photodiodes, or any other suitable means, which may be coupled to the optical coupling means 25.

The optical output 22 comprises means for converting an electrical input signal into an optical signal. The optical signal could be transmitted to the apparatus 1. The optical signal could comprise a control signal which may enable the apparatus 1 to be remotely controlled by the processing device 23. The optical signal could also be used to provide power from the processing device 23 to the apparatus 1.

The optical output could comprise one or more light emitting diodes, or any other suitable means, which may be coupled to the optical coupling means 25.

The main power source 26 comprises storage means for storing energy which may be used to power the processing device 23. The main power source 26 could comprise a chargeable battery, a capacitor or any other suitable type of energy storage means.

The main power source 26 may be coupled to the other components of the processing device 23 to enable power to be provided to the other components of the processing device 23.

In examples of the disclosure the system 21 is configured so that the main power source 26 provides power to the apparatus 1. The power could be provided to the apparatus 1 as optical signals which may be transmitted through via the optical output 22 and the optical coupling means 25.

As the main power source 26 for the system 21 is provided in the processing device 23 this reduces the size of the power source 9 needed in the apparatus 1. This also means that a user of the system 21 only needs to charge a single power source 26 to enable two separate devices to be used.

In the example shown in FIG. 2 the processing device 23 also comprises controlling circuitry 24. The controlling circuitry 24 may comprise processing circuitry and memory circuitry. The controlling circuitry 24 may comprise means for controlling the processing device 23 and/or means for providing control signals for the apparatus 1.

The controlling circuitry 24 may also provide means for processing the data obtained from the one or more sensors 3 to provide an indication of the sensed parameter and/or means for storing information indicative of the sensed parameter. For example the controlling circuitry 24 may provide means for processing the data obtained from one or more temperature sensors 3 to determine the temperature of the subject and/or means for storing information indicative of the temperature of the subject.

In the system 21 of FIG. 2 there is no direct electrical connection between the apparatus 1 and the processing device 23. The optical coupling means 25 enables data to be transferred between the sensing apparatus 1 and the processing device 23. The optical coupling means 25 may also enable power to be transferred from the main power source 26 of the processing device 23 or other main power source. As there is no direct electrical connection, this means that there are no electrical wires or other circuitry which may heat up during use and would affect the accuracy of the measurements made by the one or more sensors 3 such as temperature sensors.

In the example system 21 of FIG. 2 the apparatus 1 is comprised within a separate device to the processing device 23. This enables the apparatus 1 and the processing device 23 to be positioned in different locations. For example, when the system is in use to measure a subject's temperature the apparatus 1 could be positioned underneath the subject's armpit or on the side of their torso where an accurate and/or reliable temperature measurement may be made. The processing device 23 could be positioned on the subject's sternum or anywhere else where it may be convenient and/or comfortable to locate the processing device 23. In other examples, where the sensing apparatus 1 is configured to sense other parameters the apparatus 1 could be located in a different location.

It is to be appreciated that variations could be made to the system 21 in examples of the disclosure. For instance, in the example system 21 of FIG. 2 the apparatus 1 and the processing device 23 are provided as separate components which can be positioned in different locations. In other examples the apparatus 1 and the processing device 23 could be provided within the same device. In such examples the device comprises thermal insulation to insulate the sensing apparatus 1 from the processing device. The optical coupling means 25, which may be provided within the device, also ensures that no direct electrical connection is provided between the processing device 23 and the sensing apparatus 1.

Figure 3:
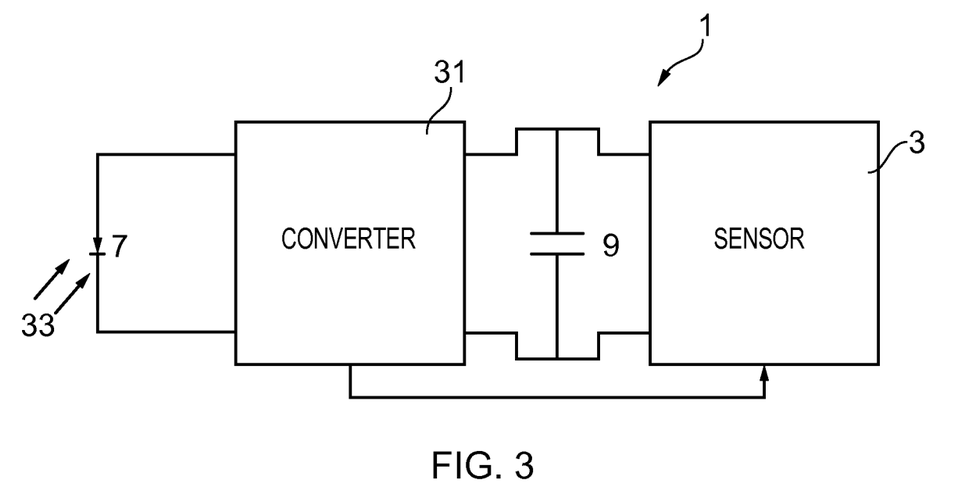
FIG. 3 illustrates components of an apparatus.

FIG. 3 illustrates components of an apparatus 1 according to examples of the disclosure. The components of the apparatus 1 shown in FIG. 3 comprises an optical input 7, a power source 9 and one or more sensors 3. The components of the apparatus 1 shown in FIG. 3 enable a measurement to be made in response to an optical input signal. It is to be appreciated that some components of the apparatus 1, such as the optical output 5 are not shown in FIG. 3.

In the example of FIG. 3 the optical input 7 comprises a photodiode. The photodiode receives an optical input signal 33 via the optical coupling means 25. The optical input signal 33 may be received from the processing device 23.

The photodiode is coupled to a direct current to direct current (DC to DC) converter 33. The DC to DC converter 33 may comprise any means configured to increase the voltage of the electrical signal provided by the photodiode in response to the optical input signal 33. The DC to DC converter 33 could comprise a charge pump or any other suitable type of DC to DC converter.

The output of the DC to DC converter is provided to the power source 9. This enables the optical energy received via the photodiode to be converted to electrical energy and stored in the power source 9. The power source 9 could be a capacitor, a low leakage capacitor, a battery or any other suitable type of power source.

In the example of FIG. 3 the one or more temperature sensors 3 comprise an integrated thermometer circuit. The integrated thermometer circuit has a low sampling frequency and low power consumption so that the circuit can be powered with the optical energy obtained via the photodiode and stored in the power source 9. Other types of sensors could be used in other examples of the disclosure. In other examples of the disclosure the sensors 3 could be configured to sense parameters other than temperature.

The output of the DC to DC converter 33 is also provided to the one or more sensors 3. The signal from the DC to DC converter 33 may trigger a measurement reading from the one or more sensors 3. In some examples the measurement may be triggered once sufficient energy has been stored in the power source 9.

The example components shown in FIG. 3 therefore enable optical power that is received by the optical input 7 to be converted to electrical energy and used to power the apparatus 1. This means that only a small power source for storing the required energy is needed within the apparatus 1. This reduces the number of components in the apparatus 1 that might heat up during use which could affect temperature measurements and/or measurements of other parameters.

Also as the power is received via optical signals there is no need to provide any electrical connections or other means between the apparatus 1 and the processing device 23 which could cause heating during use.

FIG. 4 illustrates components of an apparatus 1 according to an example of the disclosure. The components of the apparatus 1 shown in FIG. 4 comprise one or more sensors 3, an integrator 41, a comparator 43, an optical pulse generator 45 and an optical output 5. The components of the apparatus 1 shown in FIG. 4 enable an optical output signal indicative of the parameter sensed by the one or more sensors 3 to be provided. It is to be appreciated that some components of the apparatus 1, such as the optical input 7 are not shown in FIG. 3.

The example apparatus 1 in FIG. 4 comprises conversion means configured to convert the analogue output from the sensor 3 to a digital output. In the example of FIG. 4 the conversion means comprise voltage to time conversion means. Other types of conversion means could be used in other examples of the disclosure.

In the example of FIG. 4 the one or more sensors 3 comprises an analogue sensor. The analogue sensor could comprise an integrated circuit or any other suitable type of sensors. The one or more sensors 3 provide an analogue output signal where the voltage of the output signal is indicative of the sensed parameter.

The one or more sensors 3 are coupled to the integrator 41 so that the analogue output signal from the one or more sensors 3 is provided to the integrator 41. The integrator 41 comprises any means which may perform a time integration of the analogue signal obtained from the one or more sensors 3.

The integrator 41 is coupled to the comparator 43 so that the output of the integrator 41 is provided as an input to the comparator 43. The comparator 43 is configured to compare the voltage provided by the integrator 41 to a reference voltage 44. The comparator 43 provides an output indicative of the difference between the voltage provided by the integrator 41 to a reference voltage 44. The comparator may comprise a high gain differential amplifier or any other suitable means.

The comparator 43 is coupled to the pulse generator 45 so that the output of the comparator 43 is provided as an input to the pulse generator 45. The pulse generator 45 may comprise any means configured to convert the output of the comparator 43 into a pulsed signal 47. In some examples the pulse generator 45 may comprise an edge detector which may be configured to generate a pulse when a transition is detected in the input signal. Other types of pulse generator 45 may be used in other examples of the disclosure. The interval between the pulses within the pulsed signal 47 is indicative of the difference between the voltage provided by the integrator 41 to a reference voltage 44. The interval between the pulses within the pulsed signal 47 is therefore indicative of the parameter by the one or more sensors 3. In other examples the pulse generator could use pulse width encoding so that the duration of the pluses within the pulsed signal 47 is indicative of the parameter by the one or more sensors 3.

The pulse generator 45 is coupled to the optical output 5 so that the pulsed signal 47 is provided to the optical output 5. In the example of FIG. 4 the optical output 5 comprises a light emitting diode. The light emitting diode converts the pulsed signal 47 into a series of flashes of light where the duration of the flashes indicates the parameter sensed by the one or more sensors 3.

The flashes of light emitted by the light emitting diode can be transmitted to the processing device 23 via the optical coupling means 25. The processing device 23 can then determine the sensed parameter from the intervals between the received flashes of light. The processing device 23 may be configured to quantify the sensed parameter from the intervals between the received flashes of light.

In the example shown in FIG. 4 the one or more sensors 3 comprises an analogue sensor. In other examples of the disclosure a digital sensor could be used. The digital sensor could be a digital thermometer or any other suitable means.

In examples of the disclosure where a digital sensor is used the coupling means 25 and the optical input 7 may be configured to receive a control signal from the processing device 23 to control the digital sensor. In some examples the coupling means could be bi-directional to enable an output signal to be transmitted from the optical output 5 to the processing device 23 via the optical coupling means 25.

Whether the one or more sensors 3 within the apparatus 1 comprises a digital sensor or an analogue sensor may depend on a number of factors such as the processing capability of the processing device 23. The user of the analogue sensor may require more processing to be performed by the processing device 23 and so may be used in systems 21 where the processing device 23 has a higher processing capacity. Conversely the digital sensor 21 could be used in systems 21 where the processing device 23 has a lower processing capability.

Figure 5:
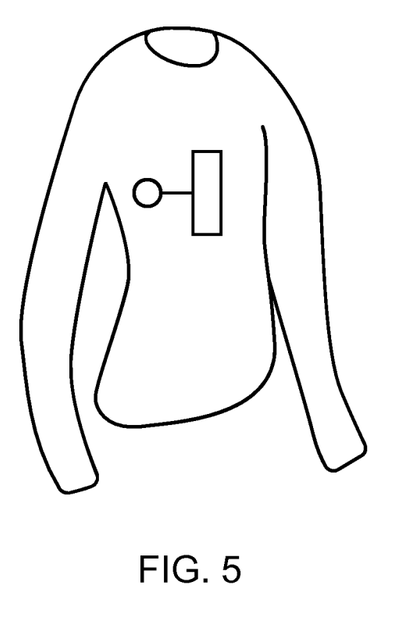
FIG. 5 illustrates a garment comprising a system.

FIG. 5 illustrates a garment 51 comprising an example sensing system 21. In the example of FIG. 5 both the apparatus 1 and the processing device 23 are provided within the same garment 51. In other examples the apparatus 1 could be provided in the garment 51 while the processing device 23 could be located elsewhere.

The garment 51 comprises an item of clothing which is configured to be worn by a subject. The subject could be a person or an animal which may require temperature measurements to be made or any other suitable parameter to be sensed. In the example of FIG. 5 the garment 51 comprises a shirt. Other items of clothing could be used in other examples of the disclosure.

In the example of FIG. 5 the apparatus 1 is positioned within the garment 51 so that when the garment 51 is worn by the subject the one or more sensors 3 are located underneath the subject's armpit or on the side of the subject's torso. In such examples the apparatus 1 may comprise one or more temperature sensors 3 configured to measure the temperature of the subject. In such examples the garment 51 may be configured so that the one or more temperature sensors 3 are located underneath the subject's armpit or on the side of the subject's torso as this may enable a reliable temperature measurement to be made.

The apparatus 1 could be located in different positions in other examples of the disclosure. For example, if the one or more sensors 3 are configured to detect environmental parameters the garment 51 may be configured so that the one or more sensors 3 are located on the chest or other suitable part of the subject which may be exposed to the environmental parameters.

In the example of FIG. 5 the processing device 23 is positioned within the garment 51 so that when the garment 51 is worn by the subject the processing device 23 is located over the subject's sternum. This could be a comfortable place for the processing device 23 to be located as the processing device 23 may be bulkier and heavier than the apparatus 1. The processing device 23 could be located in different positions in other examples of the disclosure.

An optical coupling means 25 is provided between the apparatus 1 and processing device 23. In some examples the optical coupling means 25 could be woven into the fabric of the garment 51.

In some examples additional sensors could be provided within the garment 51. The additional sensors could be configured to detect biometric signals such a bioelectric signals or biomechanical signals.

As the apparatus 1 is provided within a garment 51 which could be worn for a long period of time, for example several hours, this enables parameters relating to a subject and/or the environment of the subject to be monitored over that time period.

Examples of the disclosure provide for a sensing apparatus 1 which can provide accurate readings because the sensing apparatus 1 is thermally and electrically isolated from the processing device 23. This prevents heating caused by components of the processing device and/or the electrical connections within the processing device 23 from affecting the readings made by the one or more sensors 3. For example where the one or more sensors 3 comprise temperature sensors this will enable more accurate temperature readings to be made as they will not be affected by the heat generated by other electrical connections and/or components within the processing device 23. In some examples the temperature sensing apparatus 1 could provide temperature measurements with an accuracy of 0.1° C.

In some examples the one or more sensors 3 may comprise sensors where the ambient temperature can affect the readings made by the sensors. For example the sensors could comprise a field effect transistor (FET) or a graphene field effect transistor (GFET) where the conductivity of the channel is used to sense a parameter. However the conductivity of the channel may also be dependent upon the temperature of the sensor. Therefore, by thermally insulating the one or more sensors 3 from the processing device 23 this may enable more accurate readings to be obtained.

In some examples the processing device 23 may also comprise one or more additional sensors. The additional sensors could be configured to detect biometric parameters of the user, or any other suitable parameters. In some examples the biometric parameter could be a bioelectrical signal which could comprise at least one of an electrocardiogram signal, electroencephalogram signal, electromyogram signal, electrooculogram signal, electrogastrogram signal, galvanic skin potential or any other suitable bioelectric signal. In such examples the one or more sensors 3 can be provided in direct contact with the skin of the subject because there is no direct electrical connection between the one or more sensors 3 which could interfere with the measurement of the bioelectrical signal. This therefore may enable examples of the disclosure to be used to obtain accurate measurements of two or more parameters of the subject simultaneously. For example it may be used to obtain accurate measurements of the temperature of the subject and also a bioelectrical signal of the subject.

In some but not necessarily all examples, the processing device 23 may be configured to communicate data received from the apparatus 1 with or without local storage of the data in memory circuitry at the processing device 23 and with or without local processing of the data by circuitry or processors at the processing device 23.

The data maybe measurement data obtained by the one or sensors 3 of the apparatus 1 or data produced by the processing of measurement data from the one or more sensors 3.

The data may be stored in processed or unprocessed format remotely at one or more devices. The data may be stored in The Cloud or in any other suitable location.

The data may be processed remotely at one or more devices. The data may be partially processed locally and partially processed remotely at one or more devices.

The data may be communicated to the remote devices wirelessly via short range radio communications such as Wi-Fi or Bluetooth, for example, or over long range cellular radio links. The processing device 23 may comprise a communications interface such as, for example, a radio transceiver for communication of data.

The processing of the data, whether local or remote, may be for the purpose of health monitoring, data aggregation, patient monitoring, vital signs monitoring or other purposes.

In this description the term coupled means operationally coupled. Any number of intervening components may be provided between coupled components, including zero intervening components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus, comprising:
one or more sensors configured to sense a parameter;
an optical output configured to provide an optical output signal indicative of data obtained by the one or more sensors;
a converter between the one or more sensors and the optical output, the convertor comprising an integrator, a comparator, and a pulse generator, the integrator being configured to perform a time integration of an analog signal from the one or more sensors, the comparator being configured to compare a voltage from the integrator to a reference voltage, and the pulse generator being configured to convert an output from the comparator into a pulsed signal;
an optical input configured to receive an optical input signal and convert the optical input signal to electrical power;
a power source configured to store the electrical power obtained by the optical input and enable the electrical power to be provided to the one or more sensors and the optical output; and
an area of thermal insulation between the one or more sensors and the optical output, the optical input, and the power source;
wherein the area of thermal insulation thermally insulates the one or more sensors from the optical output, the optical input, and the power source to reduce a transfer of heat from at least one of the optical output, the optical input, or the power source to the one or more sensors;
wherein the optical output comprises one or more light emitting diodes and one or more first optical couplings where the first optical couplings are configured to couple the apparatus to a processing device to enable data obtained by the one or more sensors to be transmitted to the processing device.

2. An apparatus as claimed in claim 1 wherein the optical input comprises one or more photodiodes and a second optical coupling where the second optical coupling is configured to enable light from a processing device to be detected by the one or more photodiodes.

3. An apparatus as claimed in claim 2, wherein the second optical coupling is configured to enable light from the processing device to be transmitted to the one or more photodiodes.

4. An apparatus as claimed in claim 1 wherein the optical coupling comprises at least one bi-directional light guide.

5. An apparatus as claimed in claim 1 wherein there is no direct electrical connection between the apparatus and the processing device.

6. An apparatus as claimed in claim 1 wherein the apparatus is thermally insulated from the processing device.

7. An apparatus as claimed in claim 1 wherein the apparatus is comprised within a separate device to the processing device.

8. An apparatus as claimed in claim 1 wherein the one or more sensors comprise one or more digital sensors configured to provide a digital output.

9. An apparatus as claimed in claim 8 wherein the optical coupling is configured to receive a control signal from the processing device to control the one or more digital sensors.

10. An apparatus as claimed in claim 1 comprising a voltage to time converter configured to convert an analogue output of the one or more sensors to a digital output.

11. An apparatus as claimed in claim 1 wherein the power source comprises a super capacitor.

12. An apparatus as claimed in claim 1 wherein the one or more sensors comprises one or more temperature sensors.

13. An apparatus as claimed in claim 12 wherein the one or more temperature sensor is thermally insulated from the optical output and the optical input.

14. An apparatus as claimed in claim 1 wherein the apparatus is comprised within a wearable device.

15. An apparatus as claimed in claim 1 wherein the one or more sensors are configured to directly contact a subject in use.

16. A sensing system, comprising:
an apparatus and a processing device; the apparatus comprising:
one or more sensors configured to sense a parameter;
an optical output configured to provide an optical output signal indicative of data obtained by the one or more sensors;
a converter between the one or more sensors and the optical output, the converter comprising an integrator, a comparator, and a pulse generator, the integrator being configured to perform a time integration of an analog signal from the one or more sensors, the comparator being configured to compare a voltage from the integrator to a reference voltage, and the pulse generator being configured to convert an output from the comparator into a pulsed signal;
an optical input configured to receive an optical input signal and convert the optical input signal to electrical power;
a power source configured to store the electrical power obtained by the optical input and enable the electrical power to be provided to the one or more sensors and the optical output; and
an area of thermal insulation between the one or more sensors and the optical output, the optical input, and the power source;
wherein the area of thermal insulation thermally insulates the one or more sensors from the optical output, the optical input, and the power source to reduce a transfer of heat from at least one of the optical output, the optical input, or the power source to the one or more sensors;
wherein the optical output comprises one or more light emitting diodes and one or more optical couplings where the one or more optical couplings are configured to couple the apparatus to the processing device to enable data obtained by the one or more sensors to be transmitted to the processing device.

17. A sensing system as claimed in claim 16 wherein the processing device is comprised within a wearable device.

* * * * *